US00PP22230P3

(12) United States Plant Patent
Karniel et al.

(10) Patent No.: US PP22,230 P3
(45) Date of Patent: Nov. 8, 2011

(54) GRAPE PLANT NAMED 'ARRASIXTEEN'

(50) Latin Name: *Vitis vinifera*
Varietal Denomination: ARRASIXTEEN

(75) Inventors: Shachar Karniel, Edison, CA (US); Sal Giumarra, Edison, CA (US)

(73) Assignee: Agricultural Research and Development Limited Liability Company, Edison, CA (US)

( * ) Notice: Subject to any disclaimer, the term of this patent is extended or adjusted under 35 U.S.C. 154(b) by 0 days.

(21) Appl. No.: 12/660,741

(22) Filed: Mar. 2, 2010

(65) Prior Publication Data

US 2011/0219504 P1 Sep. 8, 2011

(51) Int. Cl.
*A01H 5/00* (2006.01)

(52) U.S. Cl. ..... Plt./207

(58) Field of Classification Search ..... Plt./205, Plt./207
See application file for complete search history.

(56) References Cited

U.S. PATENT DOCUMENTS

PP16,399 P3 4/2006 Ellis et al.
PP17,223 P3 11/2006 Giumarra et al.
PP17,224 P3 11/2006 Giumarra et al.
PP18,625 P3 3/2008 Pinhas et al.

*Primary Examiner* — Susan McCormick Ewoldt
(74) *Attorney, Agent, or Firm* — Christie, Parker & Hale, LLP

(57) ABSTRACT

A new distinct variety of grapevine named 'ARRASIXTEEN' abundantly forms attractive medium-to-large seedless berries having a Greenish/Creamy skin coloration in medium-to-large clusters. The fruit displays a sweet crisp flavor and is firm in texture. The fruit commonly is ready for harvesting during July in San Joaquin Valley of Central California, U.S.A, and displays good eating qualities as a table grape. The fruit thinness renders the fruit well amenable for handling, shipping, and storage.

1 Drawing Sheet

Classification: The present invention relates to a new *Vitis vinifera* Grapevine.

Variety denomination: The new Grapevine has the varietal denomination 'ARRASIXTEEN'.

BACKGROUND OF THE INVENTION

A breeding program was initiated during the late 90's near Bakersfield in San Joaquin Valley of Central California. In 2001, during this breeding program, a new variety of *Vitis vinifera* was created by deliberate cross breeding of two parent plants by emasculation of the pollen bearing organ of the male and introducing pollen from another male origin. The female parent of the new variety was the GV-45 seedless grape variety (non-patented in the United States). The male parent (i.e. the pollen parent) of the new variety was the Thompson seedless grape variety (non-patented in the United States).

Comparison between ARRASIXTEEN and the male parent Thompson seedless

| | ARRASIXTEEN | Thompson Seedless |
|---|---|---|
| Pruning | Spur pruning | Cane pruning |
| Leaf color | Top side: 144 A | Top side: Green 137 A |
| Berry shape | Obtuse ovoid | Cylindrical |

The parentage of the new variety can be summarized as follows:

GV-45 x Thompson seedless.

An artificial pollination was created, and the result was an embryo which possessed unique genetic qualities. The rudiments resulting from the above pollination were embryo rescued.

The plant was then transplanted to Bakersfield in San Joaquin Valley of Central California.

It was found that the new grapevine of the present invention possesses the following combination of characteristics:

(a) Forms attractive medium-to-large seedless berries having Greenish / creamy skin coloration in medium-to-large clusters which display a sweet crisp flavor, (b) Commonly bears fruit during the month of July in the San Joaquin Valley of Central California, U.S.A., and (c) Bears fruit that is firm and is well amenable for storage, handling, and shipping.

The new variety during observation to date has displayed no visible disease, and has displayed an ability to well resist cold, drought, heat; but sensitive to direct exposure to sun and wind. The fruit of the new variety has been found to display excellent handling and shipping qualities combined with desirable dessert eating qualities.

The new variety of the present invention has been found to undergo asexual propagation beginning in 2005 near Bakersfield in the San Joaquin Valley of Central California, U.S.A. by grafting on mature 'Thompson Seedless' rootstock (non-patented in the United States). Such asexual propagation has been conducted thereafter in successive years through 2008, and has shown that the characteristics of the new variety are strictly transmissible from one generation to another. Accordingly, the new variety undergoes asexual propagation in a true to type manner. The age of the plant shown in the drawing is five years old and the variety was created in 2001.

SUMMARY OF INVENTION

The new variety ARRASIXTEEN is a large, white seedless table grape with large production, e.g., about 40 to 50 bunches per vine, and an average of about two to three bunches per shoot.

Asexual reproduction by micro propagation of the new variety as performed near Bakersfield, Calif., U.S.A., at Arvin Ca. Ranch 33 which shows that the forgoing and other distinguishing characteristics come true to form and are established and transmitted through succeeding propagations.

BRIEF DESCRIPTION OF THE DRAWINGS

The accompanying photographic illustration shows typical specimens of vegetative growth of five year old specimens of the new variety, in color as nearly true as it is reasonably possible to make in a color illustration of this character. Colors in the photograph may differ from the color values cited in the detailed botanical description below, which accurately describes the colors of the new Grapevine.

FIG. 1 shows leaves, stems and grapes of 'ARRASIXTEEN'.

DETAILED BOTANICAL DESCRIPTION

The chart used in the identification of colors is The R.H.S. Colour Chart of The ROYAL HORTICULTURAL SOCIETY. The description is based on the observation of plants growing on 'Thompson Seedless' rootstock outdoors near San Joaquin Valley of Central California, U.S.A.

Vine:

*Vigor.*—Medium to strong. Medium foliage coverage.

*Productive capacity.*—25-30 tons per hectare.

*Trunk.*—Slender, includes long split strips, and six years after grafting the diameter commonly is approximately 2.4 inches (approximately 62 mm) measured 1 foot above the ground. Color of the trunk is greyed-orange (174-A).

Time of bud burst:

*Early.*—Date of bud burst in specified location of culture: Mar. 15, 2011 season in Arvin, Calif.

Young shoot:

*Openness of tip.*—Half open.

*Prostrate hairs on tip.*—Sparse.

*Anthocyanin coloration of prostrate hairs on tip.*—Weak.

*Erect hairs on tip.*—Sparse.

*Color.*—Yellow-green (144-A).

Young leaf:

*Color of upper side of blade.*—Yellow green (144-A).

*Prostrate hairs between main veins on lower side of blade.*—Sparse.

*Erect hairs on main veins on lower side of blade.*—Sparse.

Shoot:

*Attitude* (*before tying*).—Semi-erect.

*Color of dorsal side of internodes.*—Green and red; top (yellow green 145-A); bottom (grayed red 178-A).

*Color of ventral side of internodes.*—Green (yellow green 145-A).

*Color of dorsal side of nodes.*—Yellow-green (146-D).

*Color of ventral side of nodes.*—Yellow-green (146-C).

*Erect hairs on internodes.*—Absent or very sparse.

*Length of tendrils.*—3 tendrils 8.5 cm, 5.5 cm and 6 cm.

*Color of tendrils.*—Yellow green 144-C.

Flower:

*Sexual organs.*—Fully developed stamens and fully developed gynoecium.

Mature leaf:

*Size of blade.*—Small (6×5 inches).

*Shape of blade.*—Pentagonal.

*Blistering of upper side of blade.*—Absent or very weak.

*Number of lobes.*—Five.

*Depth of upper lateral sinuses.*—Medium.

*Only varieties with lobed leaves.*—Mixture of boths sides straight and both sides convex.

*Arrangement of lobes of upper lateral sinuses.*—Open.

*Arrangement of lobes of petiole sinus.*—Half open.

*Length of teeth on blade.*—3 cm.

*Ratio length/width of teeth.*—Small.

*Shape of teeth.*—Both sides straight.

*Proportion of main veins on upper side of blade with anthocyanin coloration.*—Absent or very low.

*Vein color.*—Yellow-green (145-C).

*Prostrate hairs between main veins on lower side of blade.*—Sparse.

*Erect hairs on main veins on lower side of blade.*—Medium.

*Length of petiole equal compared to length of middle vein.*—Moderately shorter; petiole: 13 cm; vein: 16 cm.

*Top side color.*—Yellow-green (146-B).

*Botton side color.*—Yellow-green (146-C).

*Texture.*—Smooth.

*Petiole color.*—Yellow-green (145-A).

*Petiole strips color.*—Greyed-red (182-B).

*Petiole length.*—13 cm.

*Vein color.*—Yellow-green (145-C).

Reproductive organs:

*Color.*—Green (141-C).

*Size.*—1.2 mm.

Time of beginning of ripening: July 30 Arvin, Calif. season

Bunch:

*Size* (*peduncle excluded*).—Large (9"×8").

*Density.*—Single berries, some pedicels visible.

*Length of peduncle primary bunch.*—Long (3").

*Average bunch weight.*—774 g.

Berry:

*Size.*—23.8 mm.

*Weight.*—14 g per berry.

*Shape.*—Obtuse ovoid.

*Color of skin* (*without bloom*).—Yellow-green (145-B).

*Ease of detachment from pedicel.*—Moderately easy.

*Thickness of skin.*—Thin.

*Anthocyanin coloration of flesh.*—Medium.

*Firmness and color of flesh.*—Very firm, yellow-green (145-D).

*Particular flavor.*—None.

*Formation of seeds.*—None.

*Berries per bunch.*—90 berries.

*Market use of the observed plant.*—Fresh market.

Woody shoot:

*Main color.*—Orange brown (grayed orange 146-B).

DNA PROFILE

To further the characterize the new Arra variety, DNA was extracted from dried leaf samples and DNA profiles were obtained in Spain, using base pairs for 14 standard microsatellite DNA markers. The data is presented hereafter.

| Microsatellite DNA Marker | Allele Sizes in Base Pairs | |
|---|---|---|
| MSV01 | 134 | 152 |
| MSV02 | 228 | 236 |
| MSV04 | 181 | 181 |
| MSV06 | 246 | 250 |
| MSV07 | 322 | 322 |
| MSV08 | 245 | 258 |
| MSV09 | 251 | 257 |
| MSV10 | 211 | 215 |
| MSV12 | 236 | 246 |
| MSV13 | 166 | 168 |
| MSV14 | 176 | 180 |
| MSV15 | 291 | 299 |

-continued

| Microsatellite DNA Marker | Allele Sizes in Base Pairs | |
|---|---|---|
| MSV16 | 186 | 188 |
| MSV17 | 159 | 159 |

The ARRASIXTEEN variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of grapevine, botanically known as *Vitis vinifera,* identified as 'ARRASIXTEEN', substantially as shown and described herein.

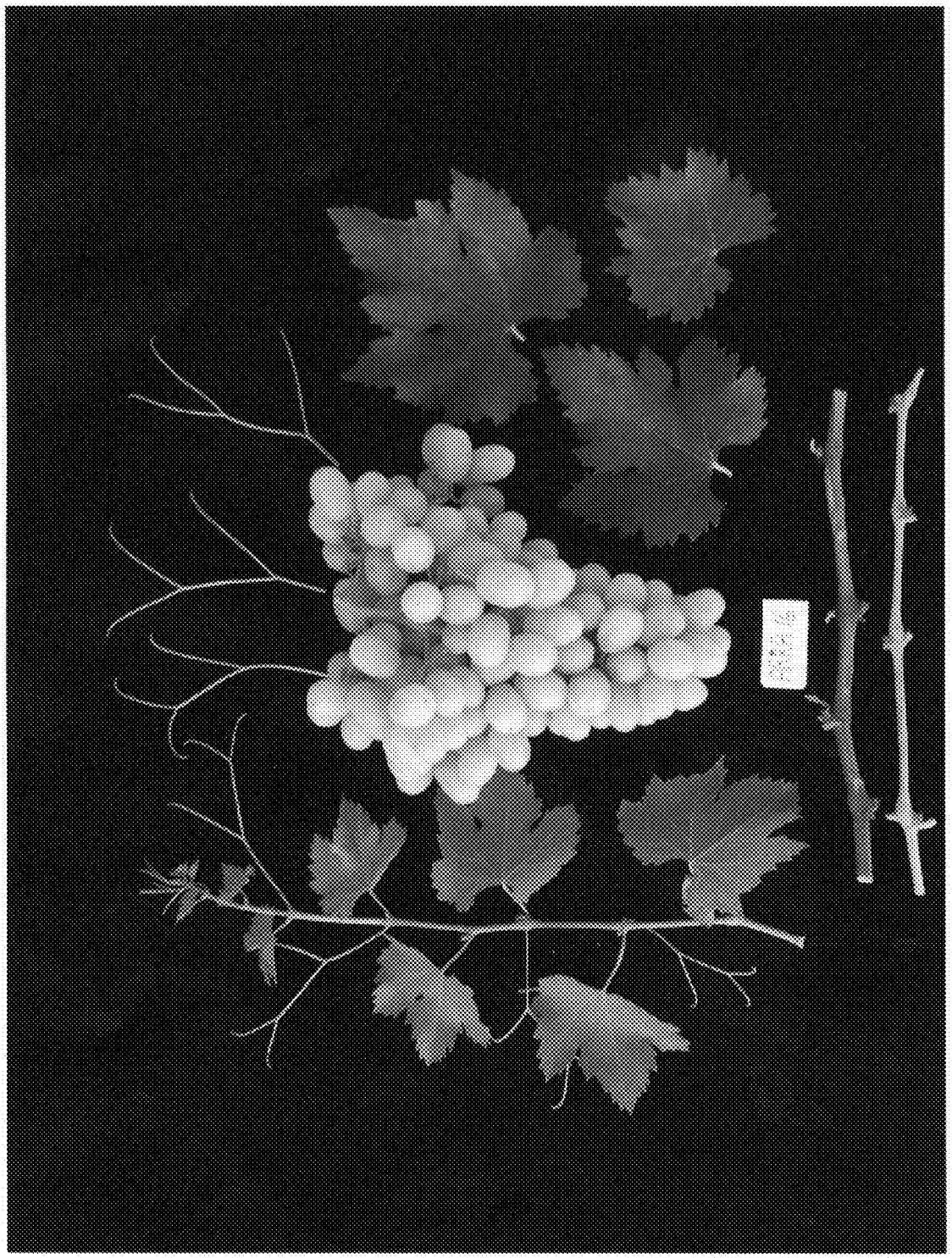

* * * * *